United States Patent [19]

Gala et al.

[11] Patent Number: 5,478,571
[45] Date of Patent: Dec. 26, 1995

[54] PROCESS FOR THE PREPARATION OF SUBSTANTIALLY ALCOHOL FREE PHARMACEUTICAL COMPOSITIONS

[75] Inventors: Pankaj B. Gala; Gary D'Alonzo, both of Somerville; Jatin J. Shah, Edison; Jay Weiss, East Brunswick, all of N.J.

[73] Assignee: Warner-Lambert Company, Morris Plains, N.J.

[21] Appl. No.: 375,077

[22] Filed: Jan. 17, 1995

Related U.S. Application Data

[63] Continuation of Ser. No. 21,428, Feb. 23, 1993, abandoned.

[51] Int. Cl.⁶ .................................................. A61K 9/14
[52] U.S. Cl. ........................ 424/464; 424/469; 424/484; 424/488; 424/489; 424/499
[58] Field of Search ................................ 424/489, 488, 424/469, 484, 499, 464

[56] References Cited

U.S. PATENT DOCUMENTS

| | | | |
|---|---|---|---|
| 4,305,502 | 2/1981 | Gregory et al. | 424/488 |
| 4,359,593 | 11/1982 | Feldman | 568/916 |
| 4,371,516 | 2/1983 | Gregory et al. | 424/488 |
| 4,684,519 | 8/1987 | Barabas | 424/78.16 |
| 4,754,597 | 7/1988 | Buxton et al. | 53/440 |
| 4,985,252 | 1/1991 | Jung et al. | 424/439 |
| 5,008,114 | 4/1991 | Lovrecich | 424/484 |
| 5,100,669 | 3/1992 | Hyon | 424/426 |
| 5,215,756 | 6/1993 | Gole et al. | 424/484 |
| 5,229,108 | 7/1983 | Solomon | 424/78.24 |

FOREIGN PATENT DOCUMENTS 287488  3/1988  European Pat. Off. ......... A61K 9/20

OTHER PUBLICATIONS

Mark et al., Kirk—Othmer Encyclopedia of Chemical Technology, vol. 3, pp. 361–363 (1978), Wiley & Sons, New York US.

*Primary Examiner*—John C. Bleutge
*Assistant Examiner*—Amy Hulina
*Attorney, Agent, or Firm*—Michael J. Atkins

[57] ABSTRACT

A novel process for the preparation of pharmaceutical compositions involving the stabilization of the active drug(s) through the reduction of residual alcohol present in a drug/carrier blend. The presence of residual alcohol in dried pharmaceutical compositions adversely affects many drugs which must be initially dissolved therein in order to achieve uniform distributions throughout the excipient carrier materials. Wherein not previously possible, its removal is achieved utilizing precise processing parameters in which water lost during the drying process is replenished during blending in a conventional solids processor.

15 Claims, No Drawings

5,478,571

PROCESS FOR THE PREPARATION OF SUBSTANTIALLY ALCOHOL FREE PHARMACEUTICAL COMPOSITIONS

This is a continuation of application Ser. No. 08/021,428 filed on Feb. 23, 1993, now abandoned.

BACKGROUND OF THE INVENTION

Pharmaceutical compositions that are orally administered for release of an active ingredient upon ingestion are usually comprised of a tablet or capsule consisting of an inert carrier material in which one or more active drugs has been incorporated. The carrier material may comprise a majority of the tablet or capsule weight and mass and serves to both protect the active ingredient during its shelf life as well as controlling its release rate during ingestion. Different excipients provide sustained, long lasting release while others may be formulated to immediately release the drug in the stomach. High potency drugs often achieve their therapeutic effects at very low doses so that a very deminimus amount of the active ingredient actually makes up the respective capsule or tablet composition. Nevertheless, uniform distribution of the drug throughout the carrier matrix is essential for proper release.

Active pharmaceutical agents may be dissolved in a solvent and then mixed with the carrier material. The solvent is then removed by drying, usually using heat, reduced pressure or a combination of both whereby the drug then becomes entrapped within or deposited on the carrier matrix. Water soluble drugs can simply be dissolved in water but water insoluble drugs must be dissolved in an organic solvent such as alcohol and the like which creates additional problems in manufacturing. Not only are the organic solvents highly volatile and thereby present a safety and health risk to those preparing the pharmaceutical compositions, but their use is also problematical from the point of drug reactivity and the need to remove all of the solvent from the composition so as to not leave any residue which may be detrimental to the pharmaceutical composition.

The removal of organic solvents in their near entirety from the pharmaceutical composition is generally a necessary step in the formulation of most pharmaceuticals. Any residue not only becomes an unwanted contaminant but may, during storage, adversely affect the active drugs potency or activity. Resins such a polyvinylpyrrolidone have been used to remove alcohol from aqueous solutions of a compound of interest, see U.S. Pat. No. 4,359,593 to Feldman, and techniques such as aeration, reduced atmospheric pressure and distillation are obviously all well known techniques in the art to achieve the same ends.

U.S. Pat. No. 4,684,519 to Barabas discloses the preparation of pharmaceutical compositions wherein the active complex is dissolved in ethanol which is then mixed with water to create an alcohol-water azeotrope. The solvent is removed by heat distillation and the active product dried. U.S. Patent Nos. 4,305,502 and 4,371,516 both to Gregory et. al disclose the preparation of an active pharmaceutical composition wherein the active is incorporated in an inert carrier by dissolving the active in a solvent, usually water, which is then removed from the composition using sublimation.

U.S. Pat. No. 4,74,597 to Buxton et. al. takes this process another step by first dissolving a water-soluble carrier material in water which is removed by sublimation so as to create an interstitial network of channels within the carrier matrix. The active, which is dissolved in a second non-aqueous solvent, is added to the carrier material and deposited in the interstitial network of channels by slowly evaporating the solvent at room temperature.

It has been found that many water insoluble drugs that necessitate their dissolution in an organic solvent are adversely effected by techniques that remove the solvent, particularly when the solvent employed reaches low levels in the drug/carrier matrix. It is an object of the present invention to provide a process that allows for the removal of substantially all the organic solvent from a drug/excipient blend, or at least to within a negligible limit, without adversely affecting the potency or stability of the actives involved. It is a further object of the present invention to uniformly disperse potent active drugs throughout a relatively large excipient/carrier blend resulting in a final product with little to no organic solvent residue. It is a further object of the present invention to provide pharmaceutical compositions of highly potent drugs in a carrier matrix that is both stable and contaminant free.

SUMMARY OF THE INVENTION

Water insoluble drugs are uniformly dispersed within an inert carrier matrix by solubilization in an organic solvent that is then mixed with the carrier excipients and dried. All of the solvent is removed without adverse affects to the drug in question. The addition of a small amount of water, approximately 2.0% when the solvent is reduced to 80% or below of its original volume in the drug carrier mixture permits the release of the final 0.3–1.0% of the solvent without destabilizing the drug of interest.

DETAILED DESCRIPTION OF THE INVENTION

There exist many water-insoluble drugs which must be dissolved in organic solvents in order to uniformly disperse them throughout an inert carrier material. Obviously however, once the dispersion has been carried out, the organic solvent must be removed whereby the dissolved drug becomes solidified as particulate matter within the matrix system. As discussed herein previously, this normally involves some type of evaporation process whereby the solvent is removed using an absorbent, heat, reduced pressure and the like. The stability of certain drugs however, is adversely affected when the residual alcohol level is not reduced below a certain point. Removal of the alcohol below this level is difficult at best however, and further complications generally arise when the small residual levels are attempted to be removed. It was surprisingly and unexpectedly discovered that the addition of a small amount of water to the drugcarrier blend prior to removal of all of the alcohol allowed for it's removal below these levels. This facilitated the manufacturing process and resulted in a substantially solvent-free pharmaceutical composition with improved drug stability.

Norethindrone acetate ((17∝)-17-Hydroxy-norpregn-4-en 20yn-3-one acetate) and ethinyl estradiol (Ethinyl-(17β)-estra-1,3,5(10)-triene-3,17-diol) are two such drugs which are potent oral contraceptives that when administered in low quantities in dosage forms are useful in hormone replacement therapy (HRT) for the treatment of many of the symptoms associated with menopause and the like. The two compounds are administered as tablets or capsules within a carrier matrix of inert compounds known in the pharmaceutical industry. Generally, the drugs are first dissolved in alcohol, preferably ethanol, or in commercially available ethanol/methanol blends and then mixed with the carrier excipients using conventional solid processing equipment known in the art. The solvent is then removed using heat, reduced pressure, or both.

It was discovered however, in actual processing conditions, the residual alcohol level could not be lowered below 0.5 to 0.6% w/w without a resultant destabilization of the drug. Whereas the destabilization of the drugs that was noted was not immediate and occurred over time, the potency of the drug was rendered such that the formulation could not be used in any kind of treatment or therapy. It was then discovered that the process of removing alcohol using a vacuum and heat results in a partial loss of the moisture that was contained in the carrier excipient blend. Generally, the moisture lost was from about 1.0% w/w to about 3.0% w/w. Without being bound to any theory, it is believed when the alcohol level is reduced to the lower limits noted, the water is also lost entrapping the alcohol in the drug-carrier matrix wherein it reacts with the actives and destablizes them.

The process of the present invention adds a small amount of water at a specific interval in the blending process which serves to draw out and replace the entrapped alcohol which can then be removed from the system. The water that is added is deminmus, roughly 2.0% w/w of blend.

The drugs and carrier materials are blended in a standard solids processor (Patterson-Kelley, East Stroudsburg, Pa.) which permits the mixing of solid materials, the addition of liquid materials thereto and their subsequent drying with no need for material transfer. An excipient blend of conventional pharmaceutical carrier materials consisting of lactose (65–70% w/w), microcrystalline cellulose (15–25% w/w) and corn starch (8–12% w/w) are first mixed in the solid processor until all three materials are uniformly dispersed. The hormone drugs are dissolved in an organic solvent such as alcohol, preferably ethanol and most preferably a methanol/ethanol blend in a ratio of approximately 1:20. The drug/alcohol solution is sprayed onto the carrier materials through an intensifier bar within the solids processor which also serves to continue to mix the pharmaceutical composition ingredients to insure a uniform distribution of drug and excipients.

The solids processor is a closed, vacuum tight vessel which can be wrapped in a hot water jacket for heating purposes. The vessel is also under reduced pressure as a vacuum is applied which together with added heat draws the alcohol solvent from the components. The drug/carrier blend is monitored until a point when approximately 80% w/w of the added alcohol has been removed from the system. When the alcohol present in the system is from between about 20% to approximately 1.5% w/w of the original amount, approximately 0.1% to about 5.0%, preferably about 2.1% water is added to the system which continues to run until nearly all the solvent(s) is removed. With subsequent drying, the amount of alcohol present in the drug carrier blend can be reduced to 0.1% or less. The dried composition can then be tabletted or encased in gelatin capsules for oral administration.

Norethindrone acetate and ethinyl estradiol are two specific drugs useful in the practice of the present invention, however, any water-insoluble drug that must be dissolved in an organic solvent such as alcohol prior to mixing in a solids processor will have improved stability if processed according to the parameters of the present invention. These drugs include, but are not limited to steroidal hormones, norgesterel (13-ethyl-17-hydroxy-18,19-dinorpregn-4-en-20yn-3-one), conjugated estrogens, norethindrone, estradiol and mixtures thereof. Whereas a blend of lactose, microcrystalline cellulose and corn starch are the preferred excipient ingredients for the carrier matrix, generally any compatible, inert pharmaceutical carrier known in the art may be used in the practice of the present invention. These again may include, but are not limited to dicalciumphosphane, tricalcium phosphate, carboxymethyl cellulose sodium, hydroxypropyl methyl cellulose, hydroxypropyl cellulose, magnesium carbonate, sodium carbonate, calcium carbonate, sugar, sorbitol, gelatinized starch and mixtures thereof.

Preferably the drug carrier mixture will comprise from about 75% to about 99% of the pharmaceutical composition and most preferably will comprise about 90% of the total amount. The organic solvent may be used in amounts of from about 1.0% to about 25% w/w and most preferably, in an amount of approximately 10% w/w. Purified water is added in an amount of from about 0.1 to about 5.1% w/w, preferably about 2.1% w/w. The pressure within the solids processor may be reduced by vacuum to about 400–760 mm mercury prior to the addition of the water and this is then raised to about 700–760 mm mercury after water addition. The temperature of the vessel should be maintained anywhere from about 10° to about 65° C., and preferably from about 38°–40° C. during the entire processing operation.

The following example is provided to better teach and disclose how to specifically carry out the process and parameters of the present invention. It is provided for illustrative purposes only and it is realized that there are many alternative embodiments that may be practiced pursuant to the directives of the present invention. The examples then, should not be perceived or interpreted as limiting the spirit and scope of the invention as recited in the claims that follow.

EXAMPLE 1

Lactose, 189.16 kg, corn starch, 28 kg and microcrystalline cellulose, 56 kg were milled through a 0.019" screen using a Comil (Quadro Engineering Inc., Waterloo, Ontario, Canada) and charged into a 20 ft$^3$ Patterson-Kelley solids processor and blended with the intensifier bar OFF for 15 minutes. Anhydrous alcohol SD 3A (40 l. heated to 38° C.) containing dissolved drugs was sprayed onto the blend over a period of 5–7 minutes through the intensifier bar with the bar and blender now turned ON. Subsequently, 6.0 l. of anhydrous alcohol SD 3A was sprayed on the blend through the intensifier bar and blended for 5 additional minutes. Drying of the blend and addition of water was carried out as follows:

| Time | Vacuum (mm) | Jacket Temperature (°C.) | Intensifier Bar | Shell rpm |
| --- | --- | --- | --- | --- |
| 0–3 hr | 625 | 38 | OFF | 1.8 |
| 3–6 hr | 690 | 38 | OFF | 1.8 |
| 6–8 hr | Maximum | 38 | OFF | 1.8 |

The vacuum at this point was then bled and the shell speed of the solids processors was increased to 14 rpm at which time 6.0 l. of purified water was added through the intensifier bar with the intensifier bar and blender on for a period of 1 minute..The mixture was blended further for an additional 4 minutes with the intensifier bar ON.

| | | | | |
| --- | --- | --- | --- | --- |
| 8–15 hr | Maximum | 38 | OFF | 1.8 |

| 15–16 hr Maximum | Cool down | OFF | 1.8 |

After the drying phase the blend was mixed at 14 rpm with the intensifier bar ON for 5 minutes. The processor was then turned off and the dry particulate composition collected, mixed with a standard lubricant and tabletted using a conventional tablet press.

What we claim is:

1. A method for the preparation of a solid pharmaceutical composition that is substantially free of any residual organic solvent comprising:
   a) solubilizing an active drug in an organic solvent;
   b) mixing the drug solution with at least one inert carrier material;
   c) removing said solvent from said drug carrier blend and adding water in the range from about 0.1% to approximately 5.0% based on the total weight of the composition to said blend when said solvent is reduced to less then half of its original amount, and;
   d) removing the remaining residual solvent to yield a dry powdered active which can be then tabletted or encapsulated.

2. The method of claim 1 wherein the amount of water to be added to said mixture ranges from about 1.5% to approximately 2.5% based on the total weight of the composition.

3. The method of claim 2 wherein said water is added to said drug-carrier blend when said organic solvent is reduced from about 50 to about 90% of its original amount.

4. The method of claim 3 wherein said water is added to said drug-carrier blend when said organic solvent is reduced from about 70% to approximately 90% of its original amount.

5. The method of claim 4 wherein said water is added to said drug-carrier blend when said remaining organic solvent is approximately 80% of its original amount.

6. The method of claim 5 wherein said organic solvent is selected from the group consisting of alcohols.

7. The method of claim 6 wherein said alcohol is selected from the group consisting of ethanol, methanol, and mixtures thereof.

8. The method of claim 7 wherein said drug is selected form the group consisting of hormone drugs and mixtures thereof.

9. The method of claim 8 wherein said hormone drugs are selected from the group consisting of steroids, oral contraceptives, estrogenic and progestational hormones and mixtures thereof.

10. The method of claim 9 wherein said oral contraceptives are selected from the group consisting of norethindrone acetate, and ethinyl estradiol and mixtures thereof.

11. The method of claim 9 wherein said alcohol is removed through the process of evaporation.

12. The method of claim 11 wherein said evaporation is carried out through the application of heat, reduced pressure or both.

13. The method of claim 12 wherein said carrier material is selected from the group consisting of lactose, microcrystalline cellulose, corn starch, dicalcium phosphate, tricalcium phosphate, carboxymethyl cellulose sodium, hydroxypropyl methyl cellulose, hydroxypropyl cellulose magnesium carbonate, sodium carbonate, calcium carbonate, sugar, sorbitol, gelatinized starch and mixtures thereof.

14. The method of claim 13 wherein said carrier material comprises a blend of from about 65–70% lactose, 15–25% microcrystalline cellulose and about 8–12% corn starch on a weight percent of the entire carrier composition.

15. A novel method for the preparation of a solid pharmaceutical composition comprising a water-insoluble drug in an inert carrier matrix comprising solubilizing the drug in alcohol, dispersing the solution throughout the inert carrier ingredients, evaporating the alcohol with heat and reduced pressure until it is substantially removed and adding water in the range from about 0.1% to approximately 5.0% based on the total weight of the composition when the alcohol is reduced to approximately 80% of its original amount followed by further heating until dry.

* * * * *